(12) United States Patent
Carlsen (10) Patent No.: US 11,686,717 B2
(45) Date of Patent: *Jun. 27, 2023

(54) DRY STICK

(71) Applicant: DELAVAL HOLDING AB, Tumba (SE)

(72) Inventor: Thomas Nikolai Carlsen, Tumba (SE)

(73) Assignee: DeLaval Holding AB, Tumba (SE)

( * ) Notice: Subject to any disclaimer, the term of this patent is extended or adjusted under 35 U.S.C. 154(b) by 377 days.

This patent is subject to a terminal disclaimer.

(21) Appl. No.: 16/769,095

(22) PCT Filed: Dec. 18, 2018

(86) PCT No.: PCT/SE2018/051337
§ 371 (c)(1),
(2) Date: Jun. 2, 2020

(87) PCT Pub. No.: WO2019/132762
PCT Pub. Date: Jul. 4, 2019

(65) Prior Publication Data
US 2021/0231629 A1 Jul. 29, 2021

(30) Foreign Application Priority Data
Dec. 28, 2017 (SE) .................................. 1751665-9

(51) Int. Cl.
*G01N 33/04* (2006.01)
*G01N 33/52* (2006.01)
(Continued)

(52) U.S. Cl.
CPC ............. *G01N 33/04* (2013.01); *G01N 33/52* (2013.01); *G01N 33/54366* (2013.01); *G01N 33/558* (2013.01)

(58) Field of Classification Search
CPC ........ G01N 33/04; G01N 33/14; G01N 33/52; G01N 33/558; G01N 35/00009; G01N 35/00019; G01N 2021/7759
(Continued)

(56) References Cited

U.S. PATENT DOCUMENTS

| 5,985,675 A | 11/1999 | Charm et al. |
| 6,180,417 B1 | 1/2001 | Hajizadeh et al. |
| (Continued) | | |

FOREIGN PATENT DOCUMENTS

| CN | 101573617 A | 11/2009 |
| CN | 104950089 A | 9/2015 |
| (Continued) | | |

OTHER PUBLICATIONS

International Search Report and Written Opinion, dated Apr. 17, 2019, from corresponding PCT application No. PCT/SE2018/051337.
(Continued)

*Primary Examiner* — Maureen Wallenhorst
(74) *Attorney, Agent, or Firm* — Nixon & Vanderhye (57) ABSTRACT

A dry stick (180a, 180b, 180c) arranged to indicate at least one biomarker value of a milk sample of an animal (100) by a lateral flow test. The dry stick (180a, 180b, 180c) includes a sample pad (310) with a reagent, configured to indicate at least one biomarker value of a received milk sample of an animal (100) by changing colours when exposed for milk having the biomarker; a porous membrane (320), configured to create a capillary flow of the milk sample, from the sample pad (310) through the porous membrane (320); an absorbent pad (330) with an absorbent configured to absorb superfluous milk from the porous membrane (320); and a porous desiccant, configured to absorb moisture from environmental air.

16 Claims, 4 Drawing Sheets (51) Int. Cl.
*G01N 33/558* (2006.01)
*G01N 33/543* (2006.01)

(58) Field of Classification Search
USPC ........ 422/400, 402, 403, 420, 430, 68.1, 66, 422/74; 436/20, 22, 23, 44, 164, 169
See application file for complete search history.

(56) References Cited

U.S. PATENT DOCUMENTS

| | | | |
|---|---|---|---|
| 8,198,073 | B2 | 6/2012 | Nygaard |
| 8,460,863 | B2 | 6/2013 | Nygaard |
| 8,617,486 | B2 | 12/2013 | Kirby et al. |
| 10,048,262 | B2 | 8/2018 | Maehana et al. |
| 10,545,146 | B2 | 1/2020 | Maehana et al. |
| 2002/0124803 | A1 | 9/2002 | Chen et al. |
| 2004/0161859 | A1 | 8/2004 | Guo et al. |
| 2007/0056873 | A1 | 3/2007 | Elorz et al. |
| 2007/0144922 | A1* | 6/2007 | Imoarai ............ G01N 33/54386 206/204 |
| 2008/0311002 | A1 | 12/2008 | Kirby et al. |
| 2009/0053829 | A1 | 2/2009 | Okamura et al. |
| 2013/0244315 | A1 | 9/2013 | Kirby et al. |
| 2014/0073062 | A1 | 3/2014 | Tamura |
| 2019/0082659 | A1 | 3/2019 | Mottram |
| 2020/0337262 | A1* | 10/2020 | Dallerup Rasmussen ................... G01N 33/04 |
| 2021/0148941 | A1* | 5/2021 | Dallerup Rasmussen ................... G01N 35/00009 |
| 2021/0231630 | A1* | 7/2021 | Dallerup Rasmussen ................... G01N 33/04 |

FOREIGN PATENT DOCUMENTS

| | | |
|---|---|---|
| CN | 105699668 A | 6/2016 |
| CN | 206657021 U | 11/2017 |
| EP | 1754971 A1 | 2/2007 |
| EP | 2863223 A1 | 4/2015 |
| WO | 88/09824 A1 | 12/1988 |
| WO | 99/47930 A1 | 9/1999 |
| WO | 2007/082545 A1 | 7/2007 |
| WO | 2017/144913 A1 | 8/2017 |

OTHER PUBLICATIONS

SE Search Report; dated SSS, from corresponding SE application No. 1751665-9.
Naik et al., "Rapid screening test for detection of oxytetracycline residues in milk using lateral flow assay", Food Chemistry, 2017, pp. 85-92, vol. 219.
Office Action issued in Chinese Patent Application No. 201880083171.1 dated Jun. 30, 2022.

* cited by examiner

DRY STICK

TECHNICAL FIELD

This document discloses a dry stick. More particularly, a dry stick is described, for measuring at least one biomarker value of a milk sample of an animal.

BACKGROUND

On an animal farm, it is important to keep the animals healthy in order to enhance milk/meat production. On a dairy farm, for example, it is very important to inseminate animals at an optimal moment in order to successfully fertilise the cow. It is important to find the right moment to inseminate each individual animal in the farm, for efficiency reasons. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance may be estimated (based on urea).

Thereby, a farmer/operator is provided with important information concerning each individual animal. However, to perform and analyse biomarker measurements of all individual animals at a farm is time consuming for the farmer. It also put high demands on administrative skills on the farmer to distinguish biomarker measurements from different animals; as well as high demands on cleanliness for not allowing a biomarker measurement of a first animal to be contaminated by biological matters of another animal.

It would for these reasons be advantageous for the farmer, if the taking of biomarker measurements on milk samples of different animals could be automated, and thereby minimising or at least reducing the manual work effort of the farmer.

It would be desired to find a way to assist the farmer in analysing his/her animals and enhance production at the farm.

SUMMARY

It is therefore an object of this invention to solve at least some of the above problems and facilitate for an operator to measure a biomarker value of a milk sample of an animal.

According to a first aspect of the invention, this objective is achieved by a dry stick arranged to indicate at least one biomarker value of a milk sample of an animal, by a lateral flow test. The dry stick comprises a sample pad, comprising a reagent, configured to indicate at least one biomarker value of a received milk sample of an animal by changing colours when exposed for milk comprising the biomarker. Further, the dry stick comprises a porous membrane, configured to create a capillary flow of the milk sample, from the sample pad through the porous membrane. In addition, the dry stick also comprises an absorbent pad, comprising an absorbent configured to absorb superfluous milk from the porous membrane; and a porous desiccant, configured to absorb moisture from environmental air.

A biomarker, or biological marker, generally refers to a measurable indicator of some biological state or condition of the animal. The biomarker value measurement may be associated with pregnancy/reproduction of the animal.

An advantage of the porous desiccant is that moisture of the environmental air could be absorbed. Thereby, by absorbing moisture, the risk of moisture affecting the functionality of the dry stick is reduced.

In a first possible implementation of the dry stick according to the first aspect, the absorbent of the absorbent pad of the dry stick may comprise cellulose fibres impregnated with the porous desiccant.

In a second possible implementation of the dry stick according to the first aspect, or according to the first possible implementation thereof, the porous desiccant of the absorbent pad may comprise silica gel.

In a third possible implementation of the dry stick according to the first aspect, or according to any previously disclosed possible implementation thereof, the porous desiccant of the absorbent pad may comprise activated clay.

In a fourth possible implementation of the dry stick according to the first aspect, or according to any previously disclosed possible implementation thereof, the porous desiccant of the absorbent pad may comprise molecular sieves.

In a fifth possible implementation of the dry stick according to the first aspect, or according to any previously disclosed possible implementation thereof, the dry stick comprises a carrying tape, upon which the sample pad, the porous membrane and the absorbent pad are arranged.

In a sixth possible implementation of the dry stick according to the first aspect, or according to any previously disclosed possible implementation thereof, the dry stick may comprise a top film, applied on the sample pad, the porous membrane and the absorbent pad, configured to keep the sample pad and the porous membrane, and the porous membrane and the absorbent pad in contact with each other.

In a seventh possible implementation of the dry stick according to the first aspect, or according to any previously disclosed possible implementation thereof, the porous membrane may comprise a nitrocellulose membrane, cellulose, a polymer, glass fibre, woven fibres, nonwoven fibres, a chromatographic gel membrane, diatomaceous earth, silica gel, silicium oxide, or kieselguhr.

In an eighth possible implementation of the dry stick according to the first aspect, or according to any previously disclosed possible implementation thereof, the sample pad may comprise a porous structure.

In a ninth possible implementation of the dry stick according to the first aspect, or according to any previously disclosed possible implementation thereof, the reagent of the sample pad may comprise particles prepared with antibodies reacting on the biomarker.

In a tenth possible implementation of the dry stick according to the first aspect, or according to any previously disclosed possible implementation thereof, the dry stick may be individually packaged on the carrying tape.

In an eleventh possible implementation of the dry stick according to the first aspect, or according to any previously disclosed possible implementation thereof, the individually comprised dry stick may be packaged between a bottom film and a top film, embracing the dry stick, sealed together by a welded seam between the bottom film and the top film.

In a twelfth possible implementation of the dry stick according to the eleventh possible implementation, the bottom film and the top film comprises polyethylene.

An advantage with using polyethylene for the bottom film and the top film, at least for the layers of the films adjacent to the dry stick, is that creation of the welded seam around the dry stick is facilitated.

In a thirteenth possible implementation of the dry stick according to the eleventh or twelfth possible implementation, the bottom film and the top film of the carrying tape comprises a respective aluminium foil.

The aluminium foil functions as a moisture barrier, blocking liquid and moisture from reaching the dry stick, thereby keeping it dry and unaffected from being soaked.

Thanks to the described aspects, by determining biomarker values of milk samples of animals on the farm, various states, e.g. related to reproduction of the animals, or various deceases or other anomalies may be determined. By keeping the dry stick on a tape in a cassette and automate the testing of the biomarker, costs, maintenance and work intensity of the operator may be minimised or at least reduced.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as a dry stick, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
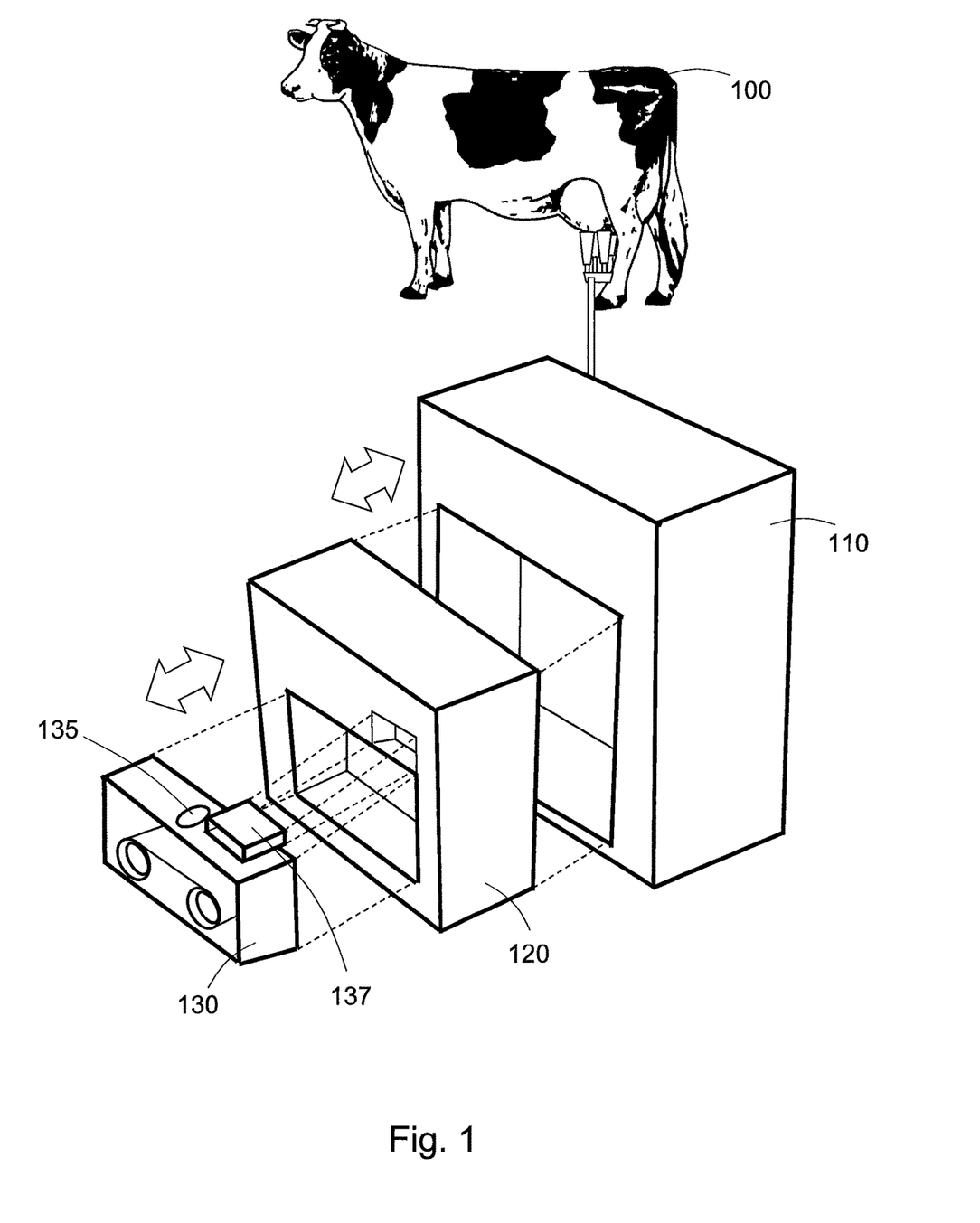
FIG. 1 illustrates an example of an arrangement for measuring a biomarker value of a milk sample of an animal.

FIG. 1 illustrates a scenario with an animal 100 which may be comprised in a herd of dairy animals at a dairy farm.

"Animal" may be any arbitrary type of domesticated female milk producing and/or meat producing mammal such as cow, goat, sheep, horse, camel, primate, dairy buffalo, donkey, yak, etc.

Milk of the animal 100 may be extracted by a milking equipment 110 such as e.g. a milking robot or other milking arrangement, and provided to a service module 120.

The service module 120 may be releasably inserted into the milking equipment 110 in some embodiments. Thus, there may be an interface between the milking equipment 110 and the service module 120 for providing milk and possibly electricity via the milking equipment 110 to the service module 120.

The service module 120 comprises various electronics and equipment such as a camera, one or several pumps, a tube element for attachment to the interface to the milking equipment 110, motors, a communication unit etc.

A cassette 130 may be detachably inserted into the service module 120. The cassette 130 comprises a tape with dry sticks, configured to indicate a biomarker value of a milk sample of the animal 100. The cassette 130 may in some embodiments be configured to be detachably inserted in the service module 120 and held in place by a fastening means such as a snap lock, a magnet, a screw, etc., and a door of the service module 120 may be closed for enclosing the cassette 130 within the service module 120, thereby further fixating the cassette 130 in the position.

Thereby, a milk sample of the animal 100 may be extracted from the animal 100 by the milking equipment and provided via the service module 120 to one of the dry sticks on the tape of the cassette 130. The dry sticks may react on presence and/or amount of one or several biomarkers, e.g. by changing colours, or intensity of a colour. The camera in the service module 120 may capture an image through an opening 135 in the cassette 130. The captured image of the dry stick may then be analysed by a control unit, and based on the intensity of the colour, presence and/or quantity of the biomarker in the milk sample may be estimated The measured biomarker may be e.g. progesterone, glycoprotein, oestrogen and/or Gonadatropin-Releasing Hormones, or any other similar biomarker associated with reproduction of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing oestrus and ovulating when pregnant. Progesterone levels, for example, may rise at the beginning of the pregnancy, and be kept at a high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the operator to detect and keep track of.

However, the measured biomarker may in some embodiments comprise LDH (Lactate Dehydrogenase), BHB (Beta-HydroxyButyrat), urea, and/or somatic cell count; or other biomarker related to status of the animal 100. In some embodiments, a plurality of the above enumerated biomarkers may be measured. Alternatively, in some embodiment, the operator may subscribe to a cassette 130 comprising a certain dry stick on the tape configured to measure a biomarker, or a set of biomarkers, as selected by the farmer; and/or different cassettes 130 comprising dry sticks on the tape configured to measure different biomarkers, or sets of biomarkers, during different periods of time of the year.

In some embodiments, a dosing module 137 may also be detachably inserted into the service module 120. The dosing module 137 may comprise for example a needle, and/or one or several pumps. A diluent container with diluent may be external to the dosing module 137.

Figures 2A, 2B:
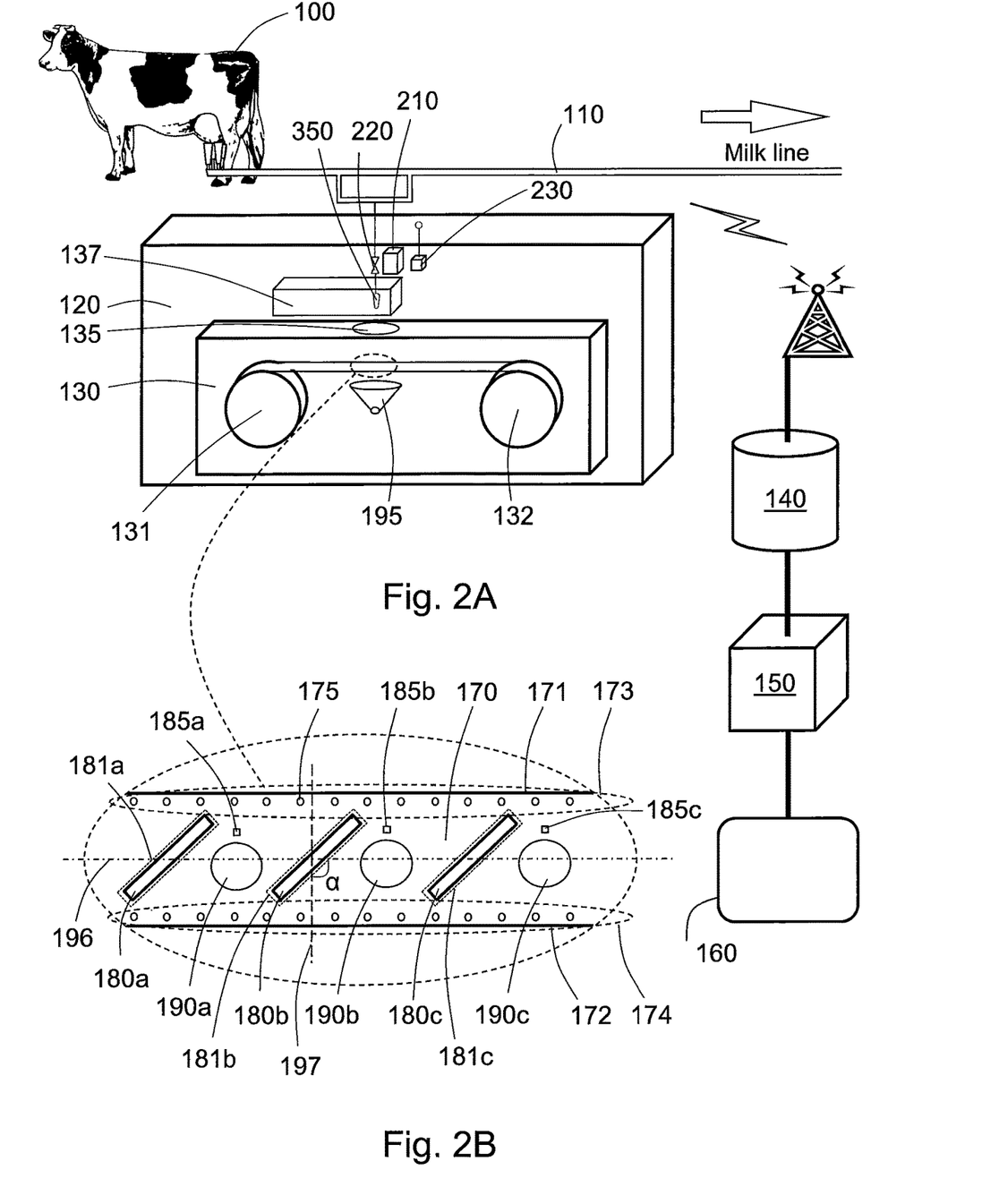
FIG. 2A illustrates a cassette inserted into a service module, according to an embodiment.
FIG. 2B illustrates a tape comprising dry sticks, according to an embodiment.
Figure 3A:
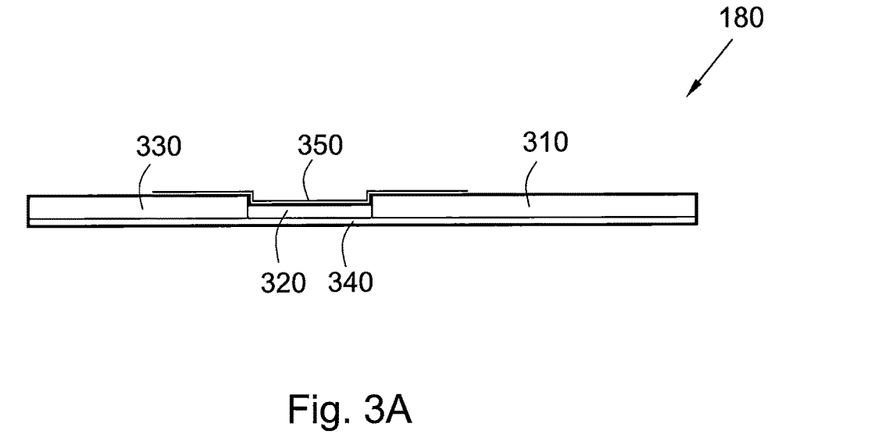
FIG. 3A illustrates a dry stick, according to an embodiment.
Figure 3B:
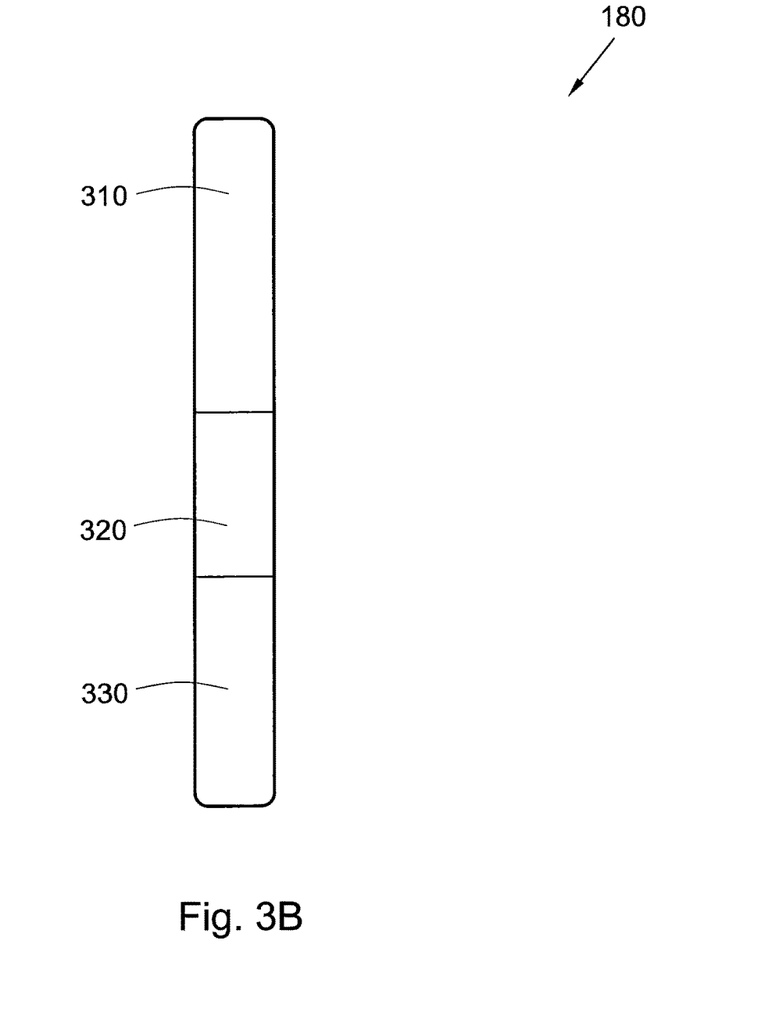
FIG. 3B illustrates a dry stick, according to an embodiment.

FIG. 1 and FIG. 2A depict general overviews of the provided solution, without going too much into details, in order for the reader to get a rough overview. Sublime examples of details of the involved entities, in particular the cassette 130 and the tape, and how they interact with each other, and how the dry sticks may be arranged may be fully enjoyed in FIG. 2B. The dry stick is depicted in FIG. 3A and FIG. 3B.

FIG. 2A illustrates a scenario illustrating a service module 120, a cassette 130, and a dosing module 137, according to an embodiment. The service module 120 comprises electronics and equipment such as e.g. a camera 210, a tube element 220 for attachment to the milking equipment, a motor, a communication unit 230, etc., to be used for determining a biometric value of a milk sample received from an animal 100. In some embodiments, the dosing module 137 may comprise one or several pumps configured to act on the tube element 220 for advancing the milk sample through the tube element 220.

In the illustrated embodiment, the dosing module 137 may comprise a needle 350 for applying the milk sample to a dry stick 180a, 180b, 180c on a tape 170 in the cassette 130 through an opening 135 in the cassette 130. The camera 210 may then align the needle 350 with the dry stick 180a, 180b, 180c on the tape 170 of the cassette 130.

The camera 210 of the service module 120 may capture an image of the dry sticks 180a, 180b, 180c of the carrier tape 170 through the opening 135, and based on these images, a cassette external motor may adjust the tape 170 for positioning a new dry sticks 180a, 180b, 180c, on which a new test is to be made, in relation to the needle 350.

The communication unit 230 may communicate via a wired or wireless communication interface, with a control unit 150, a database 140, and/or an output unit 160.

Such wireless communication interface may comprise, or at least be inspired by wireless communication technology such as Wi-Fi, 3GPP LTE, Bluetooth (BT) to name but a few possible examples of wireless communications in some embodiments.

The camera 210 of the service module 120 is configured to inspect one dry stick 180a, 180b, 180c on the tape 170 of the cassette 130, through the opening 135 of the cassette 130. The camera 210 may also assist in alignment of the needle 350 and the position of the dry stick 180a, 180b, 180c on the tape 170, by adjusting the tape 170.

Further, the service module 120 also comprises a tube element 220 configured to receive the milk sample of the animal 100 via a milking equipment and provide the milk sample to a needle 350, i.e. the needle 350 comprised in the dosing module 137.

The dosing module 137 may in addition comprise at least one pump in some embodiments, configured to act on the tube element 220 for providing the milk sample to the needle 350. The pump may thus act on the tube element 220 to get the milk sample to propagate through the tube element 220, to reach the needle 350; or the mixing chamber 355 of the needle 350. The mixing chamber 355 may alternatively be external to the needle 350.

The dosing module 137 may also comprise a liquid evacuator or drainage 195, which may collect liquid that has been output by the needle 350. The liquid, when comprising merely milk, may be returned back to the milk line in some embodiments. In other embodiments, when the milk has been mixed with diluent, the liquid may be conveyed away from the cassette 130 in order not to soak or contaminate other, unused, dry sticks 180a, 180b, 180c of the tape 170 on the cassette 130.

The control unit 150 is configured to determine a biomarker value of the milk sample of the animal 100, based on an analysis of the image, captured by the camera 210. The control unit 150 may be comprised in the service module 120 in some embodiments; or be external to the service module 120.

The database 140 may store measured biometric values of the animal 100, associated with an identity reference of the animal 100 and/or a time stamp of the measurement. Other measurements and/or data related to the animal 100 may also be stored in the database 140, such as milk yield, e.g. measured by the milk flow meter, activity, breed, parity, rumination, lactation, resting, feed intake, energy balance, Days In Milk, milk production, age and possibly other similar animal status related parameters.

The output unit 160 may be e.g. a cellular mobile telephone, a stationary or portable computing device, a computer tablet, a display, a pair of intelligent glasses, a smart contact lens, an augmented reality device, a smart watch or similar device having a user interface and wireless communication ability.

Via the output unit 160, an operator may take part of the result of the biomarker measurement of the milk sample. The operator is thereby able to analyse the status of the animal 100, such as e.g. if the animal 100 is in heat, in case progesterone is measured.

When a deviation, exceeding a first threshold limit, is detected between the outcomes of the biomarker measurement and the corresponding reference value, an alert may be outputted to the operator. The alert may comprise e.g. visual information, an audio message, a tactile signal or a combination thereof, encouraging the operator to further investigate the reasons for the detected deviation in result. In case a plurality of people is working with the herd, a broadcast may be made to the plurality of operators and their respective associated output units 160, in some embodiments.

FIG. 2B illustrates a tape 170 according to an embodiment. The cassette 130, which may be releasably inserted into the service module 120, comprises the tape 170, which in turn comprises a plurality of dry sticks 180a, 180b, 180c.

The dry sticks 180a, 180b, 180c may be arranged with an inclination α in relation to an axis 197, orthogonal to a longitudinal axis 196 of the tape 170. The inclination α may for example be 15 degrees or there about, or e.g. 10-30 degrees in some embodiments.

An opening 190a, 190b, 190c, may be arranged between at least some of the drysticks 180a, 180b, 180c, on the tape 170, or on a bottom film of the tape 170, i.e. between the welded seams 181a, 181b, 181c of at least some of the dry sticks 180a, 180b, 180c on the bottom film. The opening 190a, 190b, 190c is configured to convey liquid away from the dry sticks 180a, 180b, 180c during cleaning, or before applying the milk sample to the dry stick 180a, 180b, 180c.

Milk of a first animal 100 may contaminate a milk sample of another, subsequently tested animal. To avoid contamination, or carry over, the tubings and the needle 350 may be flushed with milk of the animal to be tested before the milk sample is applied to the dry stick 180a, 180b, 180c. For avoiding that the flushed milk of the animal to be tested soaks and/or contaminate other unused dry sticks 180a, 180b, 180c, the flushing may be made through the opening 190a, 190b, 190c of the tape 170, e.g. by lowering the needle 350 through the opening 190a, 190b, 190c, and capture the flushed milk with a liquid evacuator 195. The liquid evacuator 195 may then via a tube convey liquid away from the cassette 130.

The tape 170, or the bottom film of the tape 170 may further comprise a reference mark 185a, 185b, 185c, configured to assist a camera 210 in finding the dry stick 180a, 180*b*, 180*c*. The reference mark 185*a*, 185*b*, 185*c* may comprise e.g. a hole, a colour mark, a barcode, a simple geometry, or similar.

The reference mark 185*a*, 185*b*, 185*c* may also assist the camera 210 in determining the advancement of the top film reel, to peel off the top film of the dry stick 180*a*, 180*b*, 180*c*, enough to enable application of the milk sample to the dry stick 180*a*, 180*b*, 180*c*, while not peeling off the top film of the next dry stick 180*a*, 180*b*, 180*c*.

Further, the tape 170, or the bottom film of the tape 170 may comprise a first group 173 of advancement apertures 175, arranged at a first edge 171 of the tape 170; and a second group 174 of advancement apertures 175, arranged at a second edge 172 of the tape 170, or the bottom film of the tape 170.

Each dry stick 180*a*, 180*b*, 180*c* may be separately arranged on the tape 170, or the bottom film of the tape 170, by a welded seam 181*a*, 181*b*, 181*c*, and wherein the sealed dry sticks 180*a*, 180*b*, 180*c* are arranged on a distance from each other.

FIG. 3A and FIG. 3B illustrate a cross section of a dry stick 180*a*, 180*b*, 180*c* in an embodiment. The dry stick 180*a*, 180*b*, 180*c* is arranged to indicate at least one biomarker value of a milk sample of an animal 100 by a lateral flow test, which also may be referred to as a lateral flow immunochromatographic assay.

The dry stick 180*a*, 180*b*, 180*c* comprises a sample pad 310, comprising a reagent, configured to indicate at least one biomarker value of a received milk sample of an animal 100 by changing colours when exposed for milk comprising the biomarker.

Milk, or a liquid mix between milk and diluent may be applied on the sample pad 310.

Further, the dry stick 180*a*, 180*b*, 180*c* comprises a porous membrane 320, configured to create a capillary flow of the milk sample, from the sample pad 310 through the porous membrane 320.

The purpose of the porous membrane 320 is to absorb the milk that has been applied on the sample pad 310 by capillary force. The sample pad 310 may comprise a porous structure. The reagent of the sample pad 310 may comprise particles, such as e.g. gold particles, metal particles, latex particles, carbon, etc., prepared with antibodies reacting on the biomarker. Typically, gold nanoparticles, coloured or fluorescent latex beads dried onto conjugate pads may be used as labelling agents, resulting in high levels of variation due to instability and inconsistent release, according to some embodiments.

The biomarker value of a received milk sample may be determined by a camera taking an image of the porous membrane 320 of the dry stick 180*a*, 180*b*, 180*c*. The colour or colour nuance of the image may then be compared with a colour chart for determining presence and/or amount of the biomarker value.

The porous membrane 320 may comprise a nitrocellulose membrane, cellulose, glass fibre, polyester, rayon, a polymer, glass fibre, woven fibres, non-woven fibres, a chromatographic gel membrane, diatomaceous earth, silica gel, silicium oxide, kieselguhr, or other filtration membranes in different embodiments. The porous membrane 320 may be designed to enhance capillary pumping speed of liquid through the dry stick 180*a*, 180*b*, 180*c*.

In addition, the dry stick 180*a*, 180*b*, 180*c* also comprises an absorbent pad 330. The absorbent pad 330 comprise an absorbent configured to absorb superfluous milk from the porous membrane 320. The absorbent pad 330 also comprises a porous desiccant, configured to absorb moisture from environmental air.

Moisture in the air, during transportation or operation, may affect the outcome of the test of the biomarker, i.e. a different result than the true value may result from the test, leading to erroneous conclusions of the milk sample.

In previously known solutions, a separate, pre-packaged desiccant has been provided in a package or plastic bag. A problem therewith is that the separate desiccant, which may comprise silica gel crystals etc., may cause mechanical damage to the sensible surfaces of the dry stick 180*a*, 180*b*, 180*c*. The functionality of the dry stick 180*a*, 180*b*, 180*c* may thereby be jeopardised. By instead applying the desiccant functionality to the absorbent pad 330, it is avoided that the other surfaces of the dry stick 180*a*, 180*b*, 180*c*, i.e. the sample pad 310 and/or the porous membrane 320 are damaged by the desiccant.

The desiccant is a hygroscopic substance that induces or sustains a state of dryness, i.e. desiccation in its vicinity. The desiccant may involve chemical bonding of water molecules in some embodiments.

In some embodiments, the dry stick 180*a*, 180*b*, 180*c* may be individually sealed on the tape 170, by a welded seam 181*a*, 181*b*, 181*c*. Thereby, the dry stick 180*a*, 180*b*, 180*c* may be protected from liquid and humidity, which may affect the biomarker measurement. However, in case the sealing breaks, the desiccant of the absorbent pad 330 serves the important purpose of absorbing humidity from the environmental air. Thereby, a more reliable result of the biomarker measurement is achieved.

In some embodiments, the absorbent of the absorbent pad 330 may comprise cellulose fibres impregnated with the porous desiccant. The porous desiccant of the absorbent pad 330 may comprise e.g. silica gel, activated clay and/or molecular sieves.

The absorbent pad 330 may in some embodiments comprise a piece of paper having been treated with silica gel. Thereby, the desiccant paper of the absorbent pad 330 may offer high capacity adsorption within a semi-rigid structure. Millions of adsorbent particles may be comprised in a semi-rigid cellulose fibre matrix, which enables fast drying and extraordinary versatility in design.

Silica gel is an otherwise inert, nontoxic, water-insoluble white solid, which may be applied onto the absorbent pad 330. However, other alternative embodiments may comprise a desiccant comprising activated charcoal, calcium sulfate, calcium chloride, and molecular sieves such as e.g. zeolites.

Furthermore, the dry stick 180*a*, 180*b*, 180*c* may comprise a carrying layer 340, upon which the sample pad 310, the porous membrane 320 and the absorbent pad 330 are arranged.

Additionally, the dry stick 180*a*, 180*b*, 180*c* may comprise a top film 350, applied on the sample pad 310, the porous membrane 320 and the absorbent pad 330, configured to keep the sample pad 310 and the porous membrane 320, and the porous membrane 320 and the absorbent pad 330 in contact with each other.

Thereby, capillary force between the different areas of the dry stick 180*a*, 180*b*, 180*c* is ascertained.

Further, the dry stick 180*a*, 180*b*, 180*c* may be individually packaged on the carrying tape 170. The individually packaged dry stick 180*a*, 180*b*, 180*c* may be sealed by a welded seam 181*a*, 181*b*, 181*c*, and wherein the sealed dry stick 180*a*, 180*b*, 180*c* may be arranged at a distance from any other dry stick 180*a*, 180*b*, 180*c*.

Figure 4:
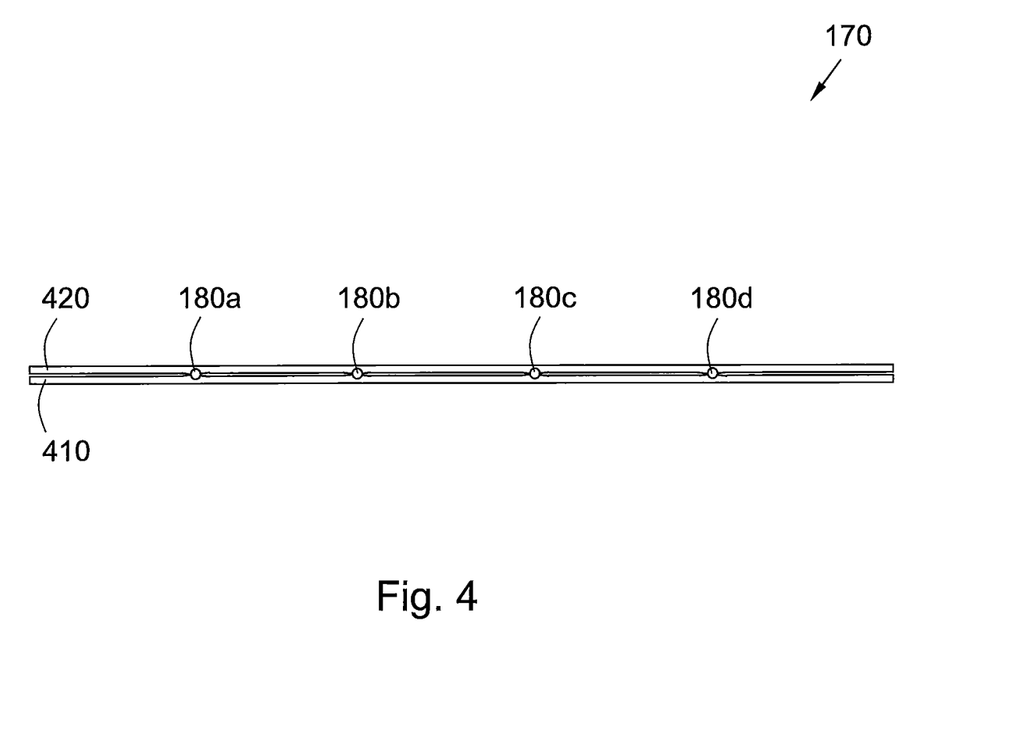
FIG. 4 illustrates a cross section of a tape comprising dry sticks, according to an embodiment.

FIG. 4 illustrates a cross section of a tape 170 according to an embodiment. The tape 170 may comprise a bottom film 410, upon which dry sticks 180a, 180b, 180c are separately arranged. The bottom film 410 may thereby constitute the carrying layer 340, in some embodiments. The dry sticks 180a, 180b, 180c may be configured to indicate at least one biomarker value of a milk sample of an animal 100. Also, the carrying tape 170 may comprise a top film 420 configured to cover the dry sticks 180a, 180b, 180c, arranged on the bottom film 410, and to be peeled off an individual dry stick 180a, 180b, 180c before application of the milk sample to the dry stick 180a, 180b, 180c.

The bottom film 410 of the carrying tape 170 may comprise a bottom layer, a medium layer and a top layer. The top film 420 of the carrying tape 170 may comprise a bottom layer, a medium layer and a top layer. The bottom layer and the top layer of the bottom film 410 and/or the top film 420 may be made of plastic while the medium layer may be made of aluminium, in some embodiments.

The aluminium foil functions as a moisture barrier, blocking liquid and moisture from reaching the dry stick, thereby keeping it dry and unaffected from being soaked. However, the aluminium foil is typically very fragile, and in case the aluminium foil is teared or otherwise damaged, it is important to keep the desiccant at the dry stick 180a, 180b, 180c in order to maintain the dry stick 180a, 180b, 180c unaffected from moisture.

The reason for applying the top film 420 is that it is important that milk from a first animal 100 does not soak the dry stick 180a, 180b, 180c on which a subsequent animal is to use for biomarker test, as the milk from the first animal may contaminate the dry stick 180a, 180b, 180c of the second animal. For this reason, the cassette 130 may further comprise a desealer, configured to remove the sealing tape from the one dry stick 180a, 180b, 180c when the one dry stick 180a, 180b, 180c is adjusted into a position aligned with the needle 350. The top film 420 may be thinner than the bottom film 410 in some embodiments, such as e.g. 10% thinner, 20% thinner, 40% thinner, etc.

The bottom film 410 may comprise a bottom layer, a medium layer and a top layer. The bottom layer and the top layer may be made of plastic, like e.g. polyethylene, polypropylene, polyamide, polyethylene terephthalate, polyethylene terephthalate polyester, polychlorotrifluoro ethylene, polyvinylidene chloride, polypropylene, polyvinyl chloride and/or polystyrene or similar material such as a thermoplastic polyester. In particular, the top layer may be made of polyethylene.

The medium layer of the bottom film 410 may be made of aluminium or an aluminium based alloy, and e.g. have a thickness between 9 µm-25 µm.

The top film 420 of the tape 170 comprise a bottom layer, a medium layer and a top layer. The bottom layer and the top layer may be made of plastic, like e.g. polyethylene, polypropylene, polyamide, polyethylene terephthalate, polychlorotrifluoro ethylene, Polyvinylidene chloride, polypropylene, polyvinyl chloride and/or polystyrene or similar material. In particular, the bottom layer may with advantage be made of polyethylene.

The layers of the bottom film 410; and the layers of the top film 420, respectively, may be laminated.

The medium layer of the top film 310 may be made of aluminium or an aluminium based alloy, and e.g. have a thickness between 9 µm-25 µm.

Using a thin layer of aluminium foil, e.g. around 9 µm, for medium layer of the bottom film 410 and/or the medium layer of the top film 420 has the advantage of allowing more (longer) tape 170 on the spools 131, 132 of the cassette 130. It is also cheaper than using a thick (i.e. around 25 µm) aluminium foil. However, using a thick aluminium foil for the medium layers makes the tape 170 less sensible to mechanical damage. A compromise may be to use a thick aluminium foil, such as about e.g. 15-25 µm for the medium layer of the bottom film 410 and a thinner aluminium foil (e.g. about 9-15 µm) for the medium layer of the top film 420, in some embodiments.

The dry sticks 180a, 180b, 180c may be maintained between the bottom film 410 and the top film 420, and be individually sealed. The individual sealing of each dry stick 180a, 180b, 180c may be made by welding the top layer of the bottom film 410 together with the bottom layer of the top film 420. Thereby, the dry sticks 180a, 180b, 180c are very well protected from milk stain, or humidity that may affect the operation of the dry sticks 180a, 180b, 180c, when they are not in turn to receive the milk sample from the needle 350. In order to facilitate the welding, the top layer of the bottom film 410 and/or the bottom layer of the top film 420 may be made of polyethylene, as polyethylene is easy to weld.

The purpose of the medium layers is to provide firmness to the tape 170, while yet allowing the tape 170 to be flexible enough to be rolled on the spools 131, 132 of the tape 170. For this purpose, the medium layers with advantage may be made of aluminium foil; or a foil made of an aluminium alloy.

The purpose of the bottom layer of the bottom film 410 is to protect the medium layer from humidity, but also from scratches and other undesired mechanical impact, as the medium layer, in particular when made of aluminium foil, is fragile and sensitive for scratches. The same may be said about the top layer of the top film 420. The bottom layer of the bottom film 410 and the top layer of the top film 420 may with advantage be made of plastic as mentioned above. The plastic also has the advantage of low friction, which ascertain a smooth running of the tape 170 when being distributed between the spools 131, 132 of the tape 170.

The embodiments, or parts thereof, illustrated in FIG. 1, FIG. 2A, FIG. 2B, FIG. 3, and/or FIG. 4 may with advantage be combined with each other for achieving further benefits.

The terminology used in the description of the embodiments as illustrated in the accompanying drawings is not intended to be limiting of the described dry stick 180a, 180b, 180c. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware, but may also be distributed in other forms such as via Internet or other wired or wireless communication system.

The invention claimed is:

1. A plurality of dry sticks (180a, 180b, 180c) arranged to indicate at least one biomarker value of a milk sample of an animal (100) by a lateral flow test,
    each of the plural dry sticks individually arranged on a bottom film (410) of a carrier tape (170),
    wherein each said dry stick (180a, 180b, 180c) comprises:
    a sample pad (310) comprising a reagent, the reagent configured to indicate at least one biomarker value of a received milk sample of an animal (100);
    a porous membrane (320) having a first edge side located in contact with an edge side of the sample pad (310), the porous membrane (320) arranged to absorb the milk that has been applied on the sample pad (310) by capillary force to create a capillary flow of the milk sample from the edge side of the sample pad (310) through the porous membrane (320),
    wherein the at least one biomarker value of the milk sample is determinable from a camera image of the porous membrane (320), a colour or colour nuance of the camera image indicating at least one of a presence and an amount of the at least one biomarker value; and
    an absorbent pad (330) located in contact with a second edge side of the porous membrane (32), the absorbent pad (330) comprising both an absorbent configured to absorb superfluous milk from the porous membrane (320) and a porous desiccant configured to absorb moisture from environmental air,
    wherein each of the plural dry sticks is individually arranged on the bottom film (410) of the carrier tape (170), with the sample pad (310), the porous membrane (320) and the absorbent pad (330) being arranged on an upper surface of the bottom film (410),
    wherein the carrier tape (170) comprises a top film (420) peelably attached to the upper surface of the bottom film (410),
    wherein the carrier tape (170) further comprises plural seals (181a, 181b, 181c) located between the top and bottom films (420, 410) of the carrier tape (170), each of the plural seals extending around and individually sealing a respective one of said plural dry sticks (180a, 180b, 180c) thereby packaging the plural dry sticks (180a, 180b, 180c) as individual dry sticks (180a, 180b, 180c) located at a distance from each other,
    wherein each of the bottom film (410) and the further top film (420) comprises a plastic,
    wherein each of the individual dry sticks (180a, 180b, 180c) is packaged between the top and bottom films (420, 410) of the carrier tape (170) within a respective one of the plural seals (181a, 181b, 181c),
    wherein each said seal is a welded seam (181a, 181b, 181c) that surrounds a different one of the dry sticks (180a, 180b, 180c), and
    wherein the top film (420) is peelable to be peeled off an individual dry stick (180a, 180b, 180c) before application of the milk sample to an individual one of the dry stick (180a, 180b, 180c) while not peeling off the top film (420) of adjacently-located unused ones of the dry sticks, (180a, 180b, 180c) with each said unused ones of said individual dry sticks (180a, 180b, 180c) not yet having application of the milk sample remaining on the bottom film (410) and covered by the top film (420) after the top film (420) has been peeled off said individual one of the dry stick (180a, 180b, 180c) such that the top film (420) protects the unused ones of the dry sticks (180a, 180b, 180c) from moisture, humidity, dirt, and mechanical damages until use.

2. The dry sticks (180a, 180b, 180c) according to claim 1, wherein the absorbent of the absorbent pad (330) comprises cellulose fibers impregnated with the porous desiccant.

3. The dry sticks (180a, 180b, 180c) according to claim 2, wherein the porous desiccant of the absorbent pad (330) comprises one of the groups consisting of silica gel, activated clay, and molecular sieves.

4. The dry sticks (180a, 180b, 180c) according to claim 2, further comprising:
    a dry stick top film (350) applied on part of a top surface of the sample pad (310), across a top surface of the porous membrane (320) and on part of a top surface of the absorbent pad (330),
    the dry stick top film (350) extending from the top surface of the sample pad (310) to the top surface of the porous membrane (320) at the first edge side of the porous membrane (320) and across the top surface of the porous membrane (320) to the top surface of the porous membrane (320) at the second edge side of the porous membrane (320), and extending to and over part of the top surface of the absorbent pad (330), the top film (350) keeping the sample pad (310) and the porous membrane (320), and the porous membrane (320) and the absorbent pad (330) in contact with each other.

5. The dry sticks (180a, 180b, 180c) according to claim 4, wherein,
    a thickness of the porous membrane (320) in a height direction of the porous membrane (320) is less than a thickness of the absorbent pad (330) in a height direction of the absorbent pad (330), and
    the thickness of the porous membrane (320) in the height direction of the porous membrane (320) is less than a thickness of the sample pad (310) in a height direction of the sample pad (310).

6. The dry sticks (180a, 180b, 180c) according to claim 1, wherein the porous desiccant of the absorbent pad (330) comprises silica gel.

7. The dry sticks (180a, 180b, 180c) according to claim 1, wherein the porous desiccant of the absorbent pad (330) comprises activated clay.

8. The dry sticks (180a, 180b, 180c) according to claim 1, wherein the porous desiccant of the absorbent pad (330) comprises molecular sieves.

9. The dry sticks (180a, 180b, 180c) according to claim 1, wherein each of the dry sticks further comprises a top film (350) applied on a top surface of the sample pad (310), a top surface of the porous membrane (320), and a top surface of the absorbent pad (330), the top film (350) configured to keep the sample pad (310) and the porous membrane (320), and the porous membrane (320) and the absorbent pad (330) in contact with each other.

10. The dry sticks (180a, 180b, 180c) according to claim 1, wherein the porous membrane (320) comprises a nitrocellulose membrane, cellulose, glass fibre, polyester, rayon, a polymer, glass fibre, woven fibres, non-woven fibres, a chromatographic gel membrane, diatomaceous earth, silica gel, silicium oxide, or kieselguhr.

11. The dry sticks (180*a*, 180*b*, 180*c*) according to claim 1, wherein the sample pad (310) comprises a porous structure.

12. The dry sticks (180*a*, 180*b*, 180*c*) according to claim 1, wherein the reagent of the sample pad (310) comprises particles prepared with antibodies reacting on the at least one biomarker.

13. The dry sticks (180*a*, 180*b*, 180*c*) according to claim 1, wherein each of the top and bottom films (420, 410) of the carrier tape (170) comprises polyethylene.

14. The dry sticks (180*a*, 180*b*, 180*c*) according to claim 1, wherein each of the top and bottom films (420, 410) of the carrier tape (170) comprises a respective aluminium foil.

15. The dry sticks (180*a*, 180*b*, 180*c*) according to claim 1,
wherein the bottom film (410) comprises an opening (190*a*, 190*b*, 190*c*) between the welded seams (181*a*, 181*b*, 181*c*) of at least some of the dry sticks (180*a*, 180*b*, 180*c*), the opening (190*a*, 190*b*, 190*c*) being configured to convey liquid away from the dry sticks (180*a*, 180*b*, 180*c*) during cleaning or before applying the milk sample to an unused one of the dry sticks (180*a*, 180*b*, 180*c*), and the further top film (420) comprises polyethylene, and wherein each of the top and bottom films (420, 410) of the carrier tape (170) comprises a respective aluminium foil.

16. The dry sticks (180*a*, 180*b*, 180*c*) according to claim 1, wherein,
a thickness of the porous membrane (320) in a height direction of the porous membrane (320) is less than a thickness of the absorbent pad (330) in a height direction of the absorbent pad (330), and the thickness of the porous membrane (320) in the height direction of the porous membrane (320) is less than a thickness of the sample pad (310) in a height direction of the sample pad (310).

\* \* \* \* \*